US006767709B1

(12) United States Patent
Suzuki et al.

(10) Patent No.: US 6,767,709 B1
(45) Date of Patent: Jul. 27, 2004

(54) IMMUNOASSAY OF HUMAN MEDULLASIN AND DIAGNOSIS OF MULTIPLE SCLEROSIS USING THE SAME

(75) Inventors: Hideaki Suzuki, Tokyo (JP); Kiyoshi Takahashi, Tokyo (JP); Hisashi Katsuragi, Tokyo (JP); Yosuke Aoki, Hino (JP)

(73) Assignee: Dainichiseika Color & Chemicals Mfg. Co., Ltd., Tokyo (JP)

( * ) Notice: Subject to any disclaimer, the term of this patent is extended or adjusted under 35 U.S.C. 154(b) by 0 days.

(21) Appl. No.: 09/715,172

(22) Filed: Nov. 20, 2000

(30) Foreign Application Priority Data

| Feb. 3, 2000 | (JP) | 2000-026828 |
| Feb. 3, 2000 | (JP) | 2000-026829 |
| Apr. 21, 2000 | (JP) | 2000-121587 |

(51) Int. Cl.$^7$ ............................................. G01N 33/53
(52) U.S. Cl. ................. 435/7.1; 435/7.24; 435/7.9; 435/70.1; 435/70.2; 435/7.94; 436/501; 436/518; 436/524; 436/536; 436/63; 436/811
(58) Field of Search .................. 435/7.1, 7.24, 435/7.9, 7.94, 70.1, 70.2; 436/501, 518, 524, 536, 63, 811

(56) References Cited

U.S. PATENT DOCUMENTS 4,745,071 A * 5/1988 Lapicola et al. .............. 436/63

FOREIGN PATENT DOCUMENTS

JP         1151085 A   *  6/1999  .......... G01N/33/53

OTHER PUBLICATIONS

Aoki et al. Clinica Chemica ACTA 178 (1988) 193–204.*
Voet et al. Biochemistry QP514.2. V64 1990 pp. 76–78, 1102, 1103.*
Hale et al. The Harper Collins Dictionary 1991 p. 262, 399, 400.*
Galfre et al. Methods in Enzymology vol. 73, pp. 1–46.*
Aoki et al. Jpn. Journal Cancer Res (Gann) 79, 687–690; Jun. 1988.*
Aoki et al. Medullasin Activity in Granulocytes of Patients with Multiple Sclerosis Ann. Neurol 15:245–249 1984.*
Biological Abstracts, vol. 78, abstract No. 37324, XP002169075, 1984.
Chemical Abstracts, vol. 134, abstract No. 204585, XP002169076, 2000.
Medline, abstract No. 20520784, XP002169074, Oct. 1, 2000.

* cited by examiner

Primary Examiner—Christopher L. Chin
Assistant Examiner—Pensee T. Do
(74) Attorney, Agent, or Firm—Birch, Stewart, Kolasch & Birch, LLP

(57) ABSTRACT

There is provided an immunoassay by which the amount of human medullasin present inside granulocytes, which are one leukocyte component in blood, can be determined with high accuracy and with good reproducibility. Also provided is an immunoassay of medullasin, wherein when measuring the medullasin in blood using an anti-human medullasin antibody, the determination of the amount of human medullasin in a blood sample using said anti-human medullasin antibody is carried out after treating the blood sample with an aqueous liquid having a specific osmotic pressure different to the osmotic pressure of blood to completely break up the leukocytes. Also provided is a method of diagnosing multiple sclerosis characterized in that the human medullasin content of a blood sample is measured using an immunoassay, and the onset of multiple sclerosis and the extent of the disease is diagnosed according to the size of, or changes in, this measured value.

14 Claims, 5 Drawing Sheets

Calibration Curve for Measurement of Human Medullasin in Blood Sample

Calibration Curve for Measurement of Human Medullasin in Blood Sample

Calibration Curve for Measurement of Human Medullasin in Blood Sample

Comparison of the Medullasin Values for Multiple Sclerosis Patients and Non-inflammatory Nervous Disease Patients

- Multiple sclerosis patients:     355 ± 117 (n=112)
- Non-inflammatory nervous disease patients: 233 ± 66 (n=80)
- Normal individuals:     213 ± 34 (n=25)

Cut-off value = 281 ($\mu g/10^8$ granulocytes)

Comparison of medullasin values between male and female multiple sclerosis patients

- Multiple sclerosis patients:
    Female:    $351 \pm 107$ (n=78)
    Male:      $367 \pm 143$ (n=34)
- Normal individuals:    $214 \pm 34$ (n=24)

Cut-off value = 281 ($\mu g/10^8$ granulocytes)

Comparison of medullasin values for multiple sclerosis patients of different age groups ○ : Female, ● : Male
- Multiple sclerosis patients:
    - 10-19: 421 ± 154 (n=9)
    - 20-29: 329 ± 94 (n=26)
    - 30-39: 357 ± 104 (n=30)
    - 40-49: 330 ± 157 (n=17)
    - 50 and over: 375 ± 125 (n=21)
- Normal individuals: 213 ± 34 (n=25)

Cut-off value = 281 ($\mu g/10^8$ granulocytes)

IMMUNOASSAY OF HUMAN MEDULLASIN AND DIAGNOSIS OF MULTIPLE SCLEROSIS USING THE SAME

FIELD OF THE INVENTION

The present invention relates to a method of immunologically measuring human medullasin in blood and a method of diagnosing multiple sclerosis using the same. In more detail, it relates to a method of immunologically measuring human medullasin in blood including a step of pretreating the blood sample in order to accurately measure the content of medullasin in the granulocytes in the blood, and to a method of diagnosing multiple sclerosis using the medullasin content in blood.

DESCRIPTION OF RELATED ART

Medullasin, which is a kind of serine protease, occurs in granulocytes etc. and is thought to widely play important roles in defense mechanism including expression of inflammation, in particular chronic inflammation. The amount of medullasin in granulocytes is increased in advanced stage of a number of chronic inflammatory diseases, and is normalized in remission stage. However, in patients suffering from multiple sclerosis, it is observed that the amount of medullasin is prominently increased a few days before the advanced stage, and is normalized before remission. Multiple sclerosis is characterized by localized demyelinated lesion in white matter of the central nerve system and gliosis. It is a serious chronic inflammatory disease which progresses with repeated remission and aggravation, and in many cases results in death in 10 to 15 years. The cause of multiple sclerosis has still not been clearly identified, but it is thought that this disease is a kind of autoimmune disease in which autoantibodies attack the nerve tissue upon stimulation of the immune system by a virus or a bacterium. Its diagnosis is quite difficult, and is presently carried out by magnetic resonance imaging (MRI) or the like. However, a method such as MRI requires a very large-scale equipment and high skill in the measuring operation and are costly. Furthermore, a method of testing bone marrow liquid has the problem of inflicting much pain on the patient. In light of these circumstances, a simple diagonosis method by which diagnosis of the disease, understanding of the state of the disease and asumption of consequence can be carried out is now being developed. As a result, study has been carried out into methods of measuring the activity of medullasin in granulocyte in blood, and together with the development of an immunological measurement method by which it can be measured easily, there has been proposed the possibility of diagnosing multiple sclerosis according to the granulocyte medullasin content in blood.

However, there has been observed the phenomenon that if, when measuring after diluting the blood-sample with an aqueous medium in a method of immnunologically measuring human medullasin, the measurement is made without carrying out a treatment to completely expel the medullasin present in the granulocyte to out of the granulocyte, the reproducibility of the measured values is not good giving rise to variation in the measured values. Accordingly, the development of a method of immunologically measuring the amount of human medullasin in blood with good reproducibility has been desired.

With respect to the question of whether multiple sclerosis can be diagnosed on the basis of the amount of medullasin in the blood, such a judgment requires the inspection of considerable amounts of clinical data. However, up to now, this kind of data has not existed, and furthermore, it has been difficult to make an accurate diagnosis because of the difficulty in obtaining an accurate measured value of medullasin in granulocyte in blood due to the large variation in the measured values. Accordingly, the diagnosis of multiple sclerosis on the basis of the amount of medullasin in the blood was difficult.

SUMMARY OF THE INVENTION

Accordingly, the inventors of the present invention have carried out extensive research into solving the above-described problem. As a result, they found that the human medullasin in blood could be accurately measured with good reproducibility by immunologically measuring the human medullasin using anti-human medullasin antibodies after completely breaking up the leukocytes by treatment of the blood sample with an aqueous liquid including a hemolysate or an aqueous liquid having a specific osmotic pressure different to the osmotic pressure of human blood.

Furthermore, with the establishment of said method for accurately measuring human medullasin with good reproducibility, the inventors of the present invention noticed that the size of and changes in the measured content of human medullasin in the blood sample are closely related to the onset of multiple sclerosis and its extent etc. It was on the basis of these findings that the present invention was arrived at.

A first aspect of the present invention relates to a method of immunologically measuring the human medullasin content in blood characterized by comprising the following steps (a) and (b):

(a) a step of breaking up the leukocytes in a blood sample by contacting said blood sample with the following aqueous liquids (i) or (ii) or an aqueous liquid mixture of (i) and (ii)
  (i) an aqueous liquid having an osmotic pressure of 250 mOsm/kg. $H_2O$ or less or an aqueous liquid having an osmotic pressure of 310 mOsm/kg.$H_2O$ or more;
  (ii) an aqueous liquid comprising a hemolysate; and (b) immunologically measuring the amount of human medullasin released into the blood sample from the leukocytes broken up in step (a) using an anti-human medullasin antibody.

A second aspect of the present invention relates to a method of diagnosing multiple sclerosis characterised by including the following steps (a), (b) and (c);

(a) a step of breaking up the leukocytes in a blood sample by contacting said blood sample with the following aqueous liquids (i) or (ii) or an aqueous liquid mixture of (i) and (ii)
  (i) an aqueous liquid having an osmotic pressure of 250 mOsm/kg. $H_2O$ or less or an aqueous liquid having an osmotic pressure of 310 mOsm/kg.$H_2O$ or more,
  (ii) an aqueous liquid comprising a hemolysate;

(b) immunologically measuring the amount of human medullasin released into the blood sample from the leukocytes broken up in step (a) using an anti-human medullasin antibody; and (c) observing the size of and/or changes in the human medullasin content in the blood measured in step (b).

DETAILED DESCRIPTION OF THE PREFERRED EMBODIMENTS

Figure 1:
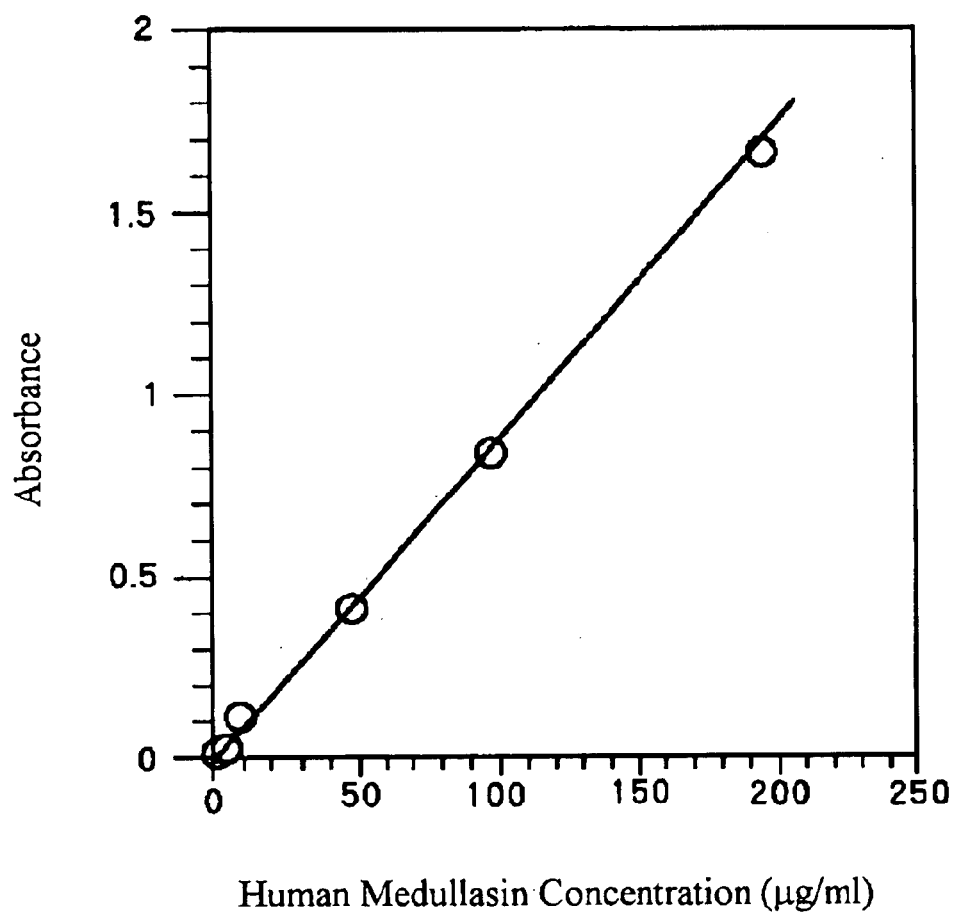
FIG. 1 is a calibration curve for measuring human medullasin, prepared by plotting the absorbance measured by the enzyme immunoassay described in Example 2 as a function of the concentration of the antigen.
Figure 2:
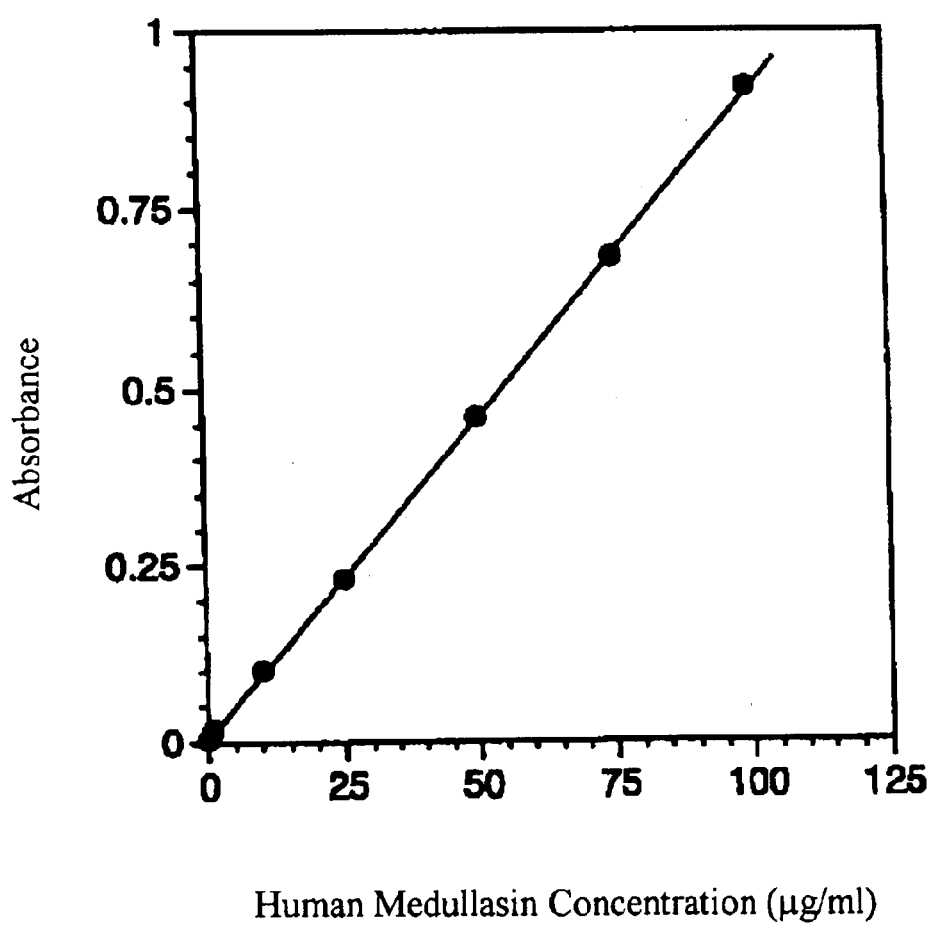
FIG. 2 is a calibration curve for measuring human medullasin, prepared by plotting the absorbance measured by the enzyme immunoassay described in Example 3 as a function of the concentration of the antigen.

Hereunder, the invention shall be described in further detail. Preferred embodiments of the present invention include (1) and (2) below.

(1) First, there is provided a method of immunologically measuring the content of human medullasin in blood including:
  (a) a step of breaking up the leukocytes in a blood sample by diluting said blood sample with the following aqueous liquids (i) or (ii) or an aqueous liquid mixture of (i) and (ii)
    (i) an aqueous liquid having an osmotic pressure of 250 mOsm/kg.$H_2O$ or less or an aqueous liquid having an osmotic pressure of 310 mOsm/kg.$H_2O$ or more;
    (ii) an aqueous liquid comprising a hemolysate;
  (b) a step of capturing the human medullasin on the labelled immune complex by contacting the blood sample containing said human medullasin released from the leukocytes broken up in step (a) with an anti-human medullasin antibody immobilized on an insoluble carrier in the presence of a labelled anti-human medullasin antibody to form a sandwith complex by an antigen-antibody reactions;
  (c) a step of measuring the activity of the label material in the complex obtained in step (b).

(2) There is also provided a method of diagnosing multiple sclerosis including:
  (a) a step of breaking up the leukocytes in a blood sample by diluting said blood sample with the following aqueous liquids (i) or (ii) or an aqueous liquid mixture of (i) and (ii)
    (i) an aqueous liquid having an osmotic pressure of 250 mOsm/kg.$H_2O$ or less or an aqueous liquid having an osmotic pressure of 310 mOsm/kg.$H_2O$ or more;
    (ii) an aqueous liquid comprising a hemolysate;
  (b) a step of capturing the human medullasin on a labelled immune complex by contacting the blood sample containing the human medullasin released from the leukocytes broken up in step (a) with an anti-human medullasin antibody immobilized to an insoluble carrier in the presence of a labelled anti-human medullasin antibody to form sandwhich a complex by an antigen-antibody reaction;
  (c) a step of measuring the activity of the label material in the complex produced in step (b);
  (d) a step of observing the size of and/or changes in the content of human medullasin in the blood sample obtained from the values for the amount of label material obtained in step (c); and
  (e) diagnosing the onset and/or extent of multiple sclerosis from the observation results obtained in step (d).

The majority of the human meduflasin in the blood sample to be measured in the present invention occurs inside the granulocytes, which are one component of the leukocytes existing in blood, and completely breaking the granulocytes to release all the medullasin to outside of the cell membrane prior to measurement is therefore an essential requirement for obtaining accurate measurements. Accordingly, if this requirement is not fully met, there are large variations in the measurements and only measured data of poor reproducibility can be obtained.

Mechanical methods, methods using ultrasound waves, and methods involving repeated freezing and thawing come to mind as methods for completely breaking up the leukocytes in the blood sample. However, the inventors of the present invention have found as a result of wide research that the following method is remarkably effective as a practical method which gives measurements of high accuracy and can be carried out with relative ease compared to the above-mentioned methods.

(1) Firstly, a method of treating the blood sample with an aqueous liquid having an osmotic pressure different to that of blood; and (2) secondly, a method of treating the blood sample with an aqueous liquid comprising a hemolysate which is a pharmaceutical with which the cell membrane of the granulocytes can be broken up under gentle conditions.

The osmotic pressure of human blood is in the range of about 280 to 290 mOsm/kg.$H_2O$, and it is thus difficult, for example, to completely break up the granulocytes in the blood using an aqueous liquid having an osmotic pressure of 250 to 310 OmOsm/kg.$H_2O$.

Accordingly, the complete break up of the granulocytes in human blood can be achieved by diluting the blood with an aqueous liquid having an osmotic pressure less than 250 mOsm/kg.$H_2O$, or an aqueous liquid having an osmotic pressure greater than 310 mOsm/kg.$H_2O$.

Aqueous liquids of this kind which can be used include pure water which may include water-soluble organic solvents, and aqueous solutions and buffer solutions that are aqueous liquids having an extremely high concentration or an extremely low concentration of a solute consisting of a water soluble substance such as salts of inorganic acids, salts of organic acids, sugars, sugar alcohols, amino acids, and proteins, and that have an osmotic pressure which can completely break up granulocytes. Specifically, sodium chloride, sodium phosphates, etc. are preferred inorganic acid salts, and sodium acetate, sodium citrate etc. are preferred organic acid salts. Furthermore, glucose and sorbitol etc. are preferred sugars and sugar alcohols. The aqueous solutions having an extremely high concentration of the above-described solute contain 0.05 mol % or greater, preferably 0.1 mol % or greater of the solute, whilst the aqueous solutions having an extremely low concentration of the above-described solute contain 0.005 mol % or less, preferably 0.001 mol % or less. The amount of the aqueous liquid used is 50 to 100,000 times that of the blood sample in terms of volume units, preferably 100 to 10,000 times, and further preferably 500 to 2000 times.

Furthermore, the method of treating the blood sample with an aqueous medium including the above-mentioned hemolysate is also preferred. Anionic surfactants such as higher fatty acid salts, alkyl arylsulfonates, alkyl sulfonates and alkyl sulfonic acid esters; cationic surfactants such as alkyl pyridinium salts, alkyl trimethyl ammonium salts, and alkyl polyoxyethylene amines; non-ionic surfactants such as polyoxyethylene alkyl phenylethers, polyoxyethylene alkylethers, and polyoxyethylene sorbitan fatty acid esters; amphoteric surfactants such alkyl betaines; natural surfactants such as saponin, lecithin and cholic acid; and biocomponents such as complements and snake venom, bee toxin and an enzyme such as protease is a non-limiting specific examples of hemolysates. These hemolysates can be used in the form of an aqueous liquid having 0.0001 to 10 weight percent, preferably 0.001 to 5 wt. %, and particularly preferably 0.005 to 1 wt. %. The aqueous liquid medium may, for example, be water or a mixed medium comprising water and a water-soluble organic solvent. The amount of the aqueous liquid used is 50 to 100000 times, preferably 100 to 10000 times, and further preferably 500 to 2000 times that of the blood sample in terms of volume units.

The immunological method of measuring human medullasin is carried out on the aqueous diluted liquid blood sample obtained by treatment of a blood sample with the above-described aqueous liquid (i) or aqueous liquid (ii) and in which the granulocytes have been completely broken up. The method comprises an immune reaction stage in which the sample for measurement is contacted with an anti-human medullasin antibody in the presence of a labelled antigen or antibody to capture the human medullasin as a labelled immune complex via an antigen-antibody reaction; and a detection stage in which the thus produced immune complex is measured using the label material present in its molecule. Any method can be used for the antigen-antibody reaction in the immune reaction stage.

Non-limiting examples of methods which can be used include:

(1) a sandwich method in which a labelled antibody is reacted with the antigen in the blood sample that is to be measured after capturing it with an antibody immobilized to an insoluble carrier;

(2) a two antibodies method in which an animal-derived antibody differing from the antibody immobilized to the insoluble carrier in the sandwich method is used, and in which a second antibody labelled with respect to this antibody is further reacted with the produced sandwich complex;

(3) a competition method in which the blood sample antigen to be measured is reacted with an antibody immobilized to an insoluble carrier in the presence of a peroxidase enzyme-labelled antigen;

(4) an agglutination-precipitation method in which the blood sample including the antigen to be measured is treated with a labelled antibody that reacts specifically with these to effect agglutination-precipitation, and then detecting the label material in the immune complex separated by centrifugal separation; and (5) a biotin-avidin method in which a labelled avidin is reacted with a biotin-labelled antibody.

When an insoluble carrier is used in the method of immunologically measuring human medullasin according to the present invention, examples of such an insoluble carrier include polymeric compounds such as polystyrene, polyethylene, polypropylene, polyester, polyacrylonitrile, fluorine resins, cross-linked dextran, and polysaccharides, as well as glass, metals, magnetic particles and combinations of these. The insoluble carrier can, for example, be used in various forms such as trays, spheres, fibres, rods, discs, vessels, cells, microplates, and test tubes. Any method can be used to immobilize the antigens or antibodies to these insoluble carriers. For example, physical adsorption methods, covalent bonding methods and ionic bonding methods can be used.

Any immunoglobulin class of antibodies can be used in the method of immunologically measuring human medullasin according to the present invention, but the use of IgG class antibodies is preferred. It is possible to use either monoclonal antibodies or polyclonal antibodies, but monoclonal antibodies are preferred. These can be used, for example, in the form of the whole antibody or as fragments such as F(ab')$_2$ and Fab. The antibodies can be obtained from any source, but the use of antibodies derived from mice, rats, rabbits, cows, goats, chickens etc. is preferred.

Next, it is preferable to use enzymes, fluorescent substances, luminescent substances and radioactive substances etc. as the label material for measuring in the detection stage the labelled immune complex of human medullasin captured in this way. Non-limiting examples include enzymes such as peroxidase, alkaline phosphatase, and β-D-galactosidase; fluorescent substances such as fluorescein isocyanate and phycobiliproteins; luminescent substances such as luminols, dioxetanes, and acridinium salts; and radioactive substances such as $^{125}$I, $^{131}$I, $^{111}$In and $^{99m}$Tc. When an enzyme is used as the label material, a substrate, and, as required, a colouring agent, a fluorescent agent or a luminescent agent, is used to measure its activity. If peroxidase is used as the enzyme, hydrogen peroxide etc. can be used as a substrate, 2,2'-azinodi[3-ethylbenzothiazoline sulfonic acid] ammonium salt (ABTS), 5-aminosalicylic acid, o-phenylene-diamine, 4-aminoantipyrine, 3,3',5,5'-tetramethylbenzidine etc. as a coloring agent, 4-hydroxyphenylacetic acid, 3-(4-hyroxyphenyl)propionic acid etc. as a fluorescent agent, and luminols, lucigenin charge transport complexes as a luminescent agent (for example, refer to International Publication No. WO00/09626). Furthermore, if alkaline phosphatase is used as the enzyme, 4-nitrophenylphosphate, 4-methylumbelliferylphosphate, cortisol-21-phosphate etc. can be used as a substrate; if β-D-galactosidase is used as the enzyme, 2-nitrophenyl-β-D-galactoside, 4-methylumbelliferyl-β-D-galactoside, 3-(2'-spiroadamantane)-4-methoxy-4-(3"-β-D-galactosyloxyphenyl)-1,2-dioxetane (AMPGD) etc. can be used as a substrate.

A preferred polyclonal antibody that can be used in the method of immunologically measuring human medullasin of the present invention is a material separated as the antibody component from an anti-human medullasin anti-blood serum obtained by the immunization of an animal according to a conventional method using human medullasin as the antigen. For example, goat anti-human medullasin-polyclonal antibodies and rabbit anti-human medullasin-polyclonal antibodies are preferably used. Monoclonal antibodies that can be used in the present invention and a method for their production are described in detail in Japanese Patent Application Laid-open No. 151085/1999.

Namely, the anti-human medullasin monoclonal antibody that can be used in the method of immunologically measuring human medullasin according to the present invention is produced by culturing hybridomas in a culture madium, which hybridomas were prepared by cell fusion between myeloma cells and antibody-producing cells recovered from an animal immunized with human medullasin extracted from granulocytes separated from the blood of a normal individual, and recovering the monoclonal antibody from the culture, or by intraperitoneally administering the hybridomas to an animal, proliferating the hybridomas in ascites, and recovering the monoclonal antibody from the ascites.

The hybridomas producing the anti-human medullasin monoclonal antibody may be produced by cell fusion method. That is, the desired monoclonal antibody-producing hybridomas may be obtained by recovering antibody-producing cells from an animal immunized with human medullasin, fusing the antibody-producing cells with myeloma cells, selectively proliferating the obtained hybridomas, screening the antibody-producing hybridomas from the obtained hybridomas, and cloning the selected hybridomas.

Examples of the above-described antibody-producing cells include spleen cells, lymph node cells, and B-lymphocytes and the like, which are obtained from an animal immunized with human medullasin, or cells or a composition containing human medullasin. Examples of the animal to be immunized are mice, rats, rabbits, goats, sheep and horses. Immunization may be carried out by, for example, subscutaneously, intramuscularly or intraperitoneally administering human medullasin of an animal which a dose of about 1 $\mu$g to 1 mg a time for 1 to 2 times a month over a period of 1 to 6 months. Collection of the antibody-producing cells may be carried out 2 to 4 days after the final immunization.

The myeloma cells may be originated from mouse, rat etc. It is preferred that the antibody-producing cells and the myeloma cells be derived from the same type of animal.

Any method of fusing the cells can be used; there are no limitations. For example, it can be carried out by mixing the antibody-producing cells and the myeloma cells in a medium such as Dalbecco's Modified Eagle Medium (DMEM) in the presence of a fusion accelerator such as polyethylene glycol.

After the cell fusion operation, the hybridomas may be selected by appropriately diluting the cells with DMEM etc., centrifuging the resultant, suspending the precipitate in a selection medium such as HAT medium, and culturing the cells therein. Antibody-producing hybridomas are then screened by enzyme immunoassay using the culture supernatant, and the selected hybridoma is cloned by limiting dilution method to obtain the hybridoma producing the anti-human medullasin monoclonal antibody.

The monoclonal antibody may be produced by culturing the thus obtained antibody-producing hybridoma in an appropriate culture medium or in an animal, and recovering the monoclonal antibody from the culture. In order to produce large amounts of monoclonal antibody, the method in which the hybridomas are intraperitoneally administered to an animal of the same species as a donor of the myeloma cells, the monoclonal antibody is accumulated in the ascites, and the monoclonal antibody is recovered from the ascites, is preferred.

Separation of the monoclonal antibody from the culture or ascites can be carried out by chromatography with a column of anion exchanger or protein A, G etc. or by fractionation with ammonium sulfate which are normally used for IgG purification.

The anti-human medullasin monoclonal antibodies obtained in this way exist as four types, designated 3F03, 3G03, 2E04 and IG12, according to the type of hybridomas used to form them. The immunoglobulin class of each of these monoclonal antibodies is IgG and the subclass is $IgG_1$, and each antibody reacts specifically with human medullasin, which is the corresponding antigen. Accordingly, the above-described anti-human medullasin monoclonal antibodies are useful for the method of immunologically measuring human medullasin of the present invention.

Next, the method of diagnosing multiple sclerosis according to the present invention involves diagnosing the onset and/or the extent or the state of multiple sclerosis on the basis of the size of or changes in the value measured for the content of human medullasin in the blood sample obtained by the above-described method of immunologically measuring human medullasin. Specifically, a method can be used in which the amount of human medullasin in $10^8$ granulocytes is calculated from the measured concentration of human medullasin in the blood sample and the measured number of granulocytes in the blood sample using the same blood sample, and the onset of multiple sclerosis is judged by comparison of the size of that value with a cut-off value (average value for a normal individual±2SD (standard deviation)), or changes in extent of the disease over time are judged by comparison of changes in the value measured over time.

Figure 4:
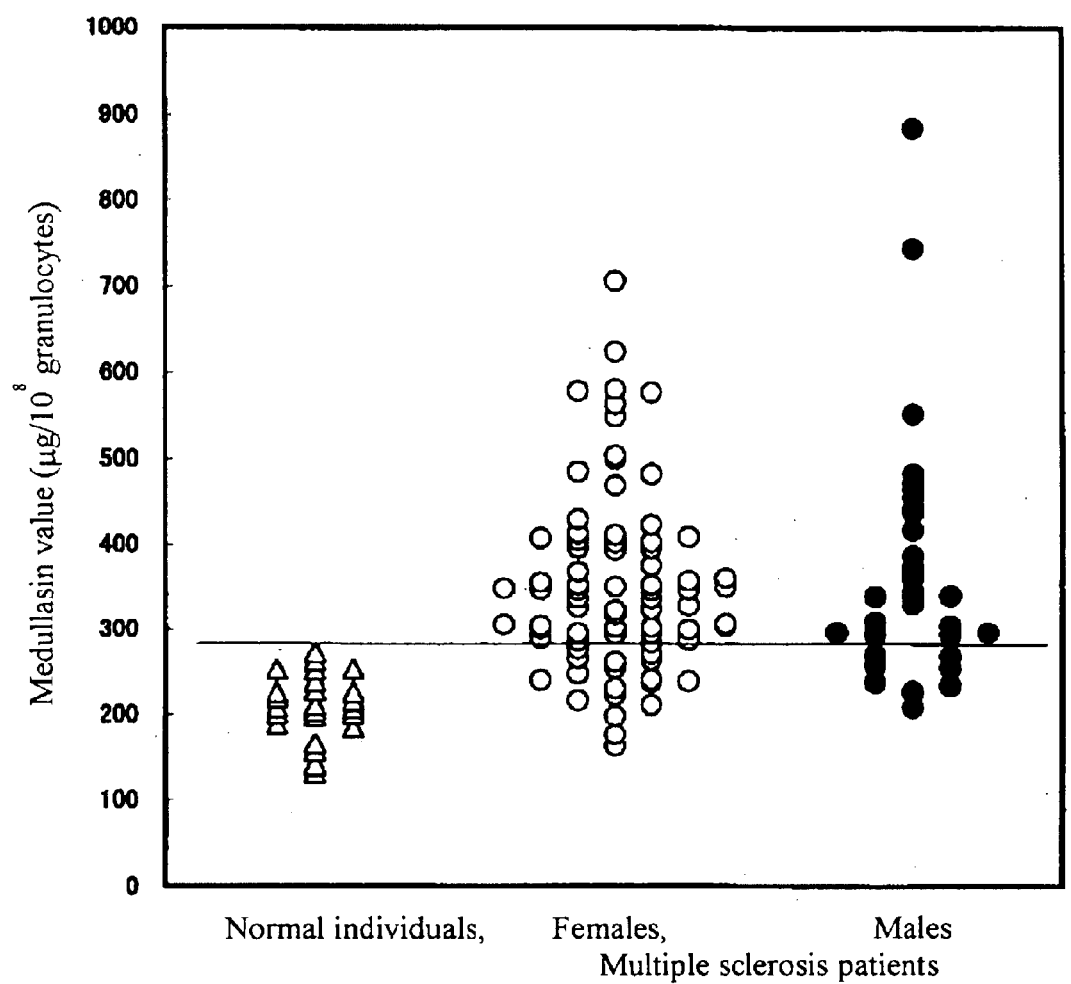
FIG. 4 shows human medullasin values ($\mu g/10^8$ granulocytes) in blood samples plotted separately for female and male patients suffering from multiple sclerosis.
Figure 5:
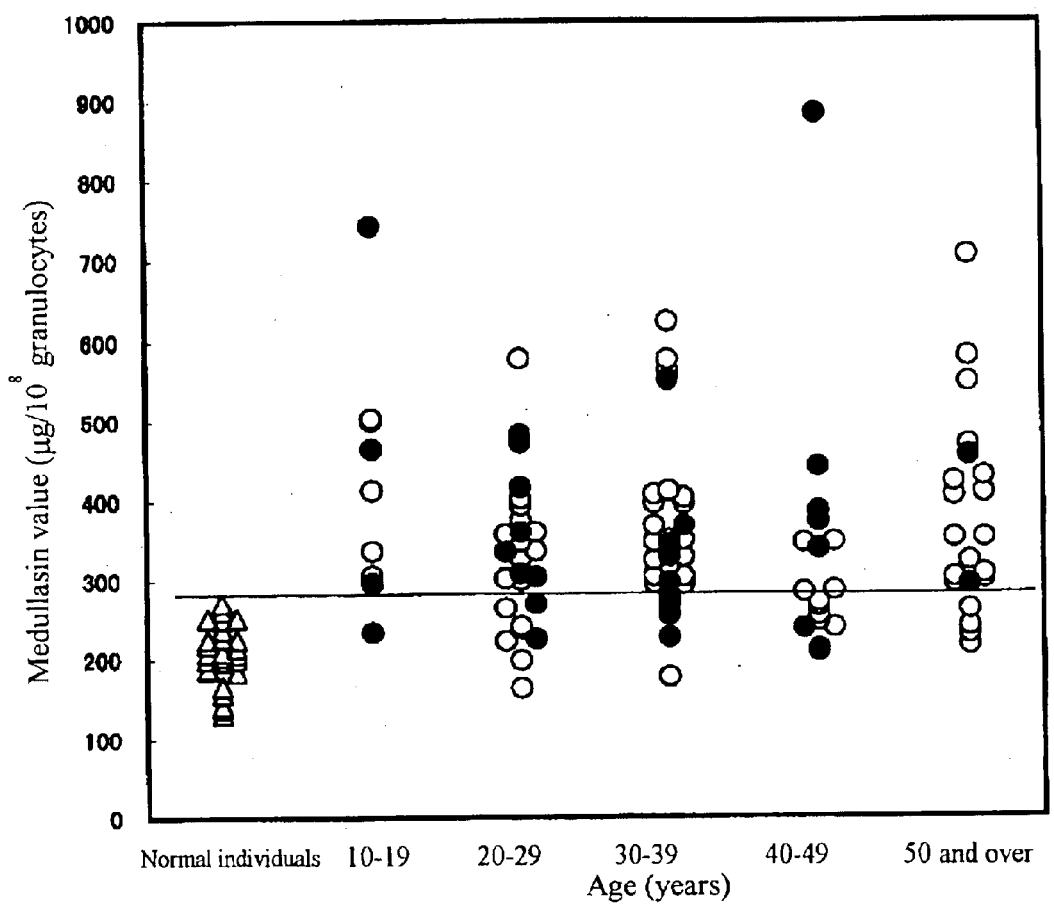
FIG. 5 shows human medullasin values ($\mu g/10^8$ granulocytes) in blood samples plotted separately for patients suffering from multiple sclerosis of different ages.

Of 112 patients suffering from multiple sclerosis who were diagnosed by this method, 85 were positive with a medullasin value no less than the cut-off value, giving a high positive percentage of 75.8%. In contrast, of 80 patients suffering from various non-inflammatory nervous diseases, the number who were positive with a medullasin value no less than the cut-off value was 13 giving a low positive percentage of 16.3%. It was thus observed that the method of diagnosing multiple sclerosis according to the human medullasin value in the blood is a diagnostic method of extremely high reliability. Furthermore, the percentage of normal individuals (in other words, healthy persons) giving a positive medullasin value was 0% (see Table 5 and FIG. 3). It was also found that the level of the medullasin value for multiple sclerosis patients does not differ between males and females (see FIG. 4) and does not differ according to age (See FIG. 5).

EXAMPLES

Hereunder, the present invention shall be described in specific terms by illustration of examples together with Reference Examples. The invention is not in any way limited by these examples. The percentages referred to in the Examples are weight percentages.

Reference Example 1

Preparation of Purified Human Medullasin

For hundred milliliters of the blood from a normal individual and 6% dextran (molecular weight: 200,000–300,000) solution in physiological saline were mixed at a ratio of blood: aqueous dextran solution=2:1, and the resulting mixutre was lightly stirred with a glass rod, followed by leaving to stand the resultant at 4–8° C. for about 1 hour. The precipitated red blood cells were removed and the obtained supernatant was centrifuged at 15,000 rpm, followed by recovering the precipitate to obtain leukocytes. To the obtained leukocytes, extraction buffer containing 1 mM disodium ethylene diamine tetraacetic acid (EDTA) and 1 mM p-chloromercurybenzoic acid (PCMB) in 1 M potassium phosphate buffer (PKB) of pH 7.0 was added and the resulting mixture was incubated under stirring at 37° C. for 20 minutes. The resultant was subjected to ultrasonication for 15 seconds to completely disrupt the cells and the resultant was incubated at 37° C. for 20 minutes, followed by centrifugation at 4° C. at 12,000 rpm for 10 minutes. The supernatant was recovered and dialyzed against distilled water. The precipitated residue was subjected to to the above-described operations several times to carry out extraction. The obtained extracted fluid was applied to a CM-Sepharose gel column equilibrated with 50 mM PKB (pH6.0) and the column was washed the same buffer. The adsorbed substances were then eluted with 1 M PKB (pH6.0) and eluted solution was dialyzed against distilled water overnight to remove salt, followed by concentrating the resultant with a collodion membrane, to obtain 1.5 mg of purified human medullasin.

Reference Example 2
Production of Anti-human Medullasin Monoclonal Antibody (1) Preparation of Hybridomas by Cell Fusion Between Antibody-Producing Cells and Myeloma Cells The human medullasin extracted and purified from human granulocytes in Reference Example 1 was emulsified with Freund's complete adjuvant and the resultant was subcutaneously administered to a BALB/C mice of 7 weeks old at a dose of 50 µg/mouse. After 4 weeks, the mice were subjected to additional immunization by the same method as the first immunization. Seven days after the additional immunization, increase in the blood level of antibodies was confirmed. Another 7 days later, the antigen was intraperitoneally administered at a dose of 50 µg/mouse at the final immunization. On the other hand, mouse myeloma P3-X63-Ag8-U1 (P3U1) cells were passaged in a Dalbecco's Modified Eagle's Medium (DMEM) supplemented with 20% fetus calf serum. Three days after final immunization, fused spleen cells were collected from the mice and with P3U1 cells using polyethylene glycol 4000 and the resultant was placed in wells of a 96-well microplate. After cell fusion operation, the medium was changed to DMEM supplemented with 100 µM hypoxanthine, 0.4 µM aminopterin, and 16 µM thymidine (HAT medium), and hybridomas between the spleen cells and the myeloma cells were obtained by selective culture for 2 to 3 weeks.

(2) Screening of Anti-human Medullasin Antibody-Producing Hybridomas

The titers of the antibodies in the culture fluids of the hybridomas were determined by ELISA (enzyme linked immunosorbent assay), thereby carrying out screening. Namely, human medullasin was adsorbed on the walls of a microplate for ELISA, and the wells were blocked with 2% bovine serum albumin (BSA) solution in 10 mM phosphate-buffered saline (PBS) (pH 7.4). Fifty microliters of the hybridoma culture fluid was added to each well and the resultant was left to stand for 1 hour. After removing the hybridoma culture washing the wells. 100 µl of 2 µg/ml solution of peroxidase-labelled goat anti-mouse IgG-Fc antibody in PBS was added to each well, the resulting mixture was allowed to react at 37° C. for 1 hour. After removing the enzyme-labelled antibody solution and washing the wells, 200 µl of a 0.1M phosphate citrate buffer solution (pH4.6) containing 0.05% ABTS and 0.0034% hydrogen peroxide was added to generate color thereby selecting anti-human medullasin antibody-producing hybridoma.

(3) Cloning of Antibody-Producing Cells and Preparation of Monoclonal Antibodies Each of the cultures of the anti-human medullasin antibody-producing hybridomas was subjected to cloning by the limiting dilution method to finally obtain 4 kinds of monoclonal hybridomas. The hybridomas were separately administered to BALB/C mice intraperitoneally which mice preliminarily received pristane and the hybridomas were grown to obtain ascites each containing the monoclonal antibody. Next, to the obtained ascites, 50% saturated ammonium sulfate was added to precipitate the antibody. The precipitate was separated, dissolved in PBS. The resulting solution was to dialyzed against 50 mM Tris-Hydrochloric acid buffer solution (pH 7.8) containing 3M NaCl. It was then applied to a Protein A-Sepharose CL4B column (commercially available from Pharmacia). The adsorbed antibody was eluted by 0.1M glycine-HCl buffer solution (pH 5.0), and the eluted solution was neutralized, followed by purification of antibody therefrom to obtain 4 kinds of monoclonal antibody, 3F03, 3G03, 2E04 and 1G12.

(4) Properties of the Monoclonal Antibodies

Western Blotting

The antigen corresponding to the monoclonal antibodies was immobilized by Western Blotting Method.

First, medullasin from human granulocytes was subjected to SDS-polyacrylamide gel electrophoresis. The protein was transferred from the slab gel to a nitrocellulose sheet over a period of 2 hours at a voltage slope of 7V/cm using a solution containing 25 mM Tris (hydroxymethyl) aminomethane, 192 mM glycine and 20% methanol added to an electrolytic solution buffer. Next, each lane on the nitrocellulose sheet was cut and one of the sheets was subjected to protein staining with Amideblack and the other sheet was subjected to enzyme immunoassay as follows. Namely, after blocking the sheet with 2% BSA/PBS, the mouse anti-human medullasin monoclonal antibody was added as a primary antibody, and then peroxidase-labelled goat anti-mouse IgG-Fc specific antibody was added as a secondary antibody, and the resultant was allowed to react. After washing the sheet, a substrate solution containing 0.04% 3,3'-diaminobenzidine and 0.0034% hydrogen peroxide in PBS was added to generate colour. By this it was confirmed that all of the four mouse anti-human medullasin monoclonal antibodies recognized medullasin derived from human granulocytes.

Inhibition Assay

Human medullasin immobilized on the wells of microplate for ELISA was reacted with a biotinylated first antibody in the presence of a non-labelled second antibody, and then avidin-conjugated peroxidase was reacted, followed by addition of a substrate solution to generate color, thereby carrying out inhibition assay. By this, with any combination of the monoclonal antibodies, the amount of the reacted biotinylated antibody was not changed. Therefore, it was confirmed that the 4 monoclonal antibodies recognize epitopes (antigen sites) which are different each other.

Example 1
Preparation of Calibration Curves for Measuring Human Medullasin (1) Preparation of Beads Having Monoclonal Antibody Immobilized thereto.

After well washing polystyrene beads (6 mm diameter), the beads were immersed for one day and night at a temperature of 4° C. in a PBS (pH 7.4) solution containing 10 µg/ml of mouse anti-human medullasin monoclonal antibody (2E04). They were then washed with PBS and subjected to blocking treatment by being left in a 1% BSA aqueous solution at a temperature of 4° C. for 1 day and night to obtain beads having monoclonal antibody immobilized thereto.

(2) Preparation of Peroxidase-labelled Monoclonal Antibody

To 1.0 mg/ml solution of mouse anti-human medullasin monoclonal antibody (2E04) in a PBS solution, 0.1 ml of a 10 mg/ml solution of N-(m-maleimide benzoic acid)-N-succinimide ester (MBS) in dimethylformamide was added and the mixture was allowed to react at a temperature of 25° C. for 30 minutes. Next, this reaction mixture solution was subjected to a column packed with Sephadex G-25 and gel permeation chromatography was carried out using 0.1M phosphate buffer solution (pH6.0) to separate maleimide-bound monoclonal antibody from the unreacted MBS.

In the meantime, an ethanol solution having a concentration of 10 mg/ml of N-succinimidyl-3-(2-pyridylthio) propionate (SPDP) was added to a PBS solution having 1.0 mg/ml of horse raddish peroxidase as the peroxidase enzyme and reacted at a temperature of 25° C. for 30 minutes. Next, the reaction mixture solution was applied to a Sephadex G-25 column and subjected to gel permeatoin with 10 mM acetate buffer solution (pH4.5). The fractions containing pyridyl disulfide-bound HRP were collected, and this was concentrated by about ten-fold under ice cooling in a collodion back. To this was added 1 ml of 0.1M acetate buffer physiological saline solution (pH 4.5) containing 0.1 M dithiothreitol followed by stirring for 30 minutes at a temperature of 25° C. to reduce the pyridyl disulfide groups introduced into the HRP molecule. This reaction mixture solution was then subjected to gel pearmeation chromatography using a column packed with Sephadex G-25 and a fraction containing thiolated HRP was obtained.

Then, the maleimide-bound monoclonal antibody and the thiolated HRP were mixed and the mixture was concentrated to a protein concentration of 4 mg/ml in a collodion bag in ice cooling. After leaving the resultant to stand at 4° C. for one day, the resultant was subjected to gel pearmeation chromatography using a column packed with Ultrogel AcA44 (made by SEPRACOR), and a peroxidase enzyme-labelled monoclonal antibody was obtained.

(3) Sandwich Enzyme Immunoassay of Human Medullasin

One bead on which the mouse anti-human medullasin monoclonal antibody (3F03) was immobilized, 50 µl of 2% BSA-containing PBS solution containing purified human medullasin (standard reference material) in a concentration of 0, 1, 10, 100 or 200 ng/ml, and 350 µl of 2% BSA-containing PBS solution were placed and the mixture was incubated at 37° C. for 30 minutes.

Next, after the solution inside the test tube was removed by aspriration, the bead was washed with physiological saline solution and then the test tube was filled with 400 µl of PBS solution containing 2% BSA and containing HRP-labelled mouse anti-human meduflasin monoclonal antibody (2E04) in a concentration of 0.2 µg/ml followed by incubation at a temperature of 37° C. for 30 minutes. The solution in the test tube was removed by aspriation followed by washing with physiological saline solution. 400 µl of 0.1M phosphoric acid buffer solution (pH 4.6) containing 0.0034% hydrogen peroxide and 0.05% ABTS was then added to each test-tube, followed by incubation at 37° C. for 30 minutes. 1 ml of 0.1N aqueous oxalic acid solution was added to each test tube as a reaction terminator to stop the enzyme reaction. Next, the absorbance at a wavelength of 420 nm was measured for the resulting solution using a spectrophotometer. By plotting the measured absorbance with respect to the concentration of the standard reference material, a calibration curve with good concentration dependence as shown in FIG. 1 was obtained.

Example 2
Measurement of Medullasin in Clinical Samples by Enzyme Immunoassay

Samples of frozen blood collected from a normal individual (a healthy pereson) and from a patient suffering from multiple sclerosis were thawed at room temperature and 10 µl of each sample was added to 2 ml of distilled water (osmotic pressure=0 mOsm/kg.H$_2$O) and adequately mixed using a Voltex mixer to obtain sample solutions. 10 µl thereof was then added to test tubes, and was diluted by the addition of 390 µl of PBS solution (pH 7.4) containing 2% BSA. Next, beads having mouse anti-human medullasin monoclonal antibody (3F03) immobilized thereto were added one each to these test tubes and incubated at a temperature of 37° C. for 30 minutes. After removal of the solutions in the test tubes by aspiration, they were washed with physiological saline solution. The test tubes were then filled with 400 µl of PBS solution containing 2% BSA and containing HRP-labelled mouse anti-human medullasin monoclonal antibody (2E04) in a concentration of 0.2 µg/ml followed by incubation at a temperature of 37° C. for 30 minutes. Next, washing, enzyme reaction and reaction termination were carried out by exactly the same operations as in the preparation of the calibration curves described earlier. The absorbance at a wavelength of 420 nm was then measured using a spectrophotometer, and the human medullasin concentration was determined from the calibration curve. The measurement operation starting from the sample dilution treatment were repeated for each 5 times for the purpose of studying the reproducibility of the measurements. As a result, it was confirmed that the human medullasin concentration measured for the blood samples showed extremely good reproducibility as shown in Table 1.

TABLE 1

Measured values for human medullasin in blood

| Measurement Number | Measured Value (µg/ml) | |
|---|---|---|
| | Normal Individual | Patient |
| 1 | 8.2 | 37.2 |
| 2 | 8.0 | 35.9 |
| 3 | 8.2 | 35.5 |
| 4 | 7.9 | 36.4 |
| 5 | 8.2 | 35.8 |
| Average | 8.1 | 36.2 |
| Variation Coefficient (%) | 1.7 | 1.8 |

Comparative Example 1
Measurement of Medullasin in Clinical Samples by Enzyme Immunoassay Blood samples which had been respectively taken from a normal individual and a patient suffering from multiple sclerosis and frozen for storage were thawed by returning them to room temperature. 10 µl thereof was taken and added to 2 ml of PBS solution (pH 7.4) (osmotic pressure= 290 mOsm/kg.H$_2$O) and uniformly mixed to obtain sample solutions. 10 µl thereof was then added to test tubes, and was diluted by the addition of 390 µl of PBS (pH 7.4) containing 2% BSA. Next, beads having mouse anti-human medullasin monoclonal antibody (3F03) immobilized thereto were added one each to these test tubes and incubated at a temperature of 37° C. for 30 minutes. After removal of the solutions in the test tubes by aspiration, they were washed with physiological saline solution. The test tubes were then filled with 400 µl of PBS solution containing 2% BSA and containing HRP-labelled mouse anti-human medullasin monoclonal antibody (2E04) in a concentration of 0.2 µg/ml followed by incubation at a temperature of 37° C. for 30 minutes. Next, washing, enzyme reaction and reaction termination were carried out by exactly the same operations as in the preparation of the calibration curves described earlier. The degree of absorbance at a wavelength of 420 nm was then measured using a spectrophotometer, and the human medullasin concentration was determined from the calibration curve. The measurement operations starting from the sample dilution treatment were carried out for each 5 times for the purpose of studying the reproducibility of the measurements. As a result, it was confirmed that the human medullasin concentration measured for the blood samples gave data whose reproducibility could not always be described as good as shown in Table 2.

TABLE 2

Measured values for human medullasin in blood

| Measurement | Measured Value (µg/ml) | |
| --- | --- | --- |
| Number | Normal Individual | Patient |
| 1 | 7.8 | 28.8 |
| 2 | 6.6 | 25.2 |
| 3 | 7.1 | 27.0 |
| 4 | 5.9 | 21.6 |
| 5 | 6.9 | 26.3 |
| Average | 6.9 | 25.8 |
| Variation Coefficient (%) | 10.1 | 10.4 |

Example 3
Measurement of Medullasin in Clinical Sample by Enzyme Immunoassay

Blood samples which had been respectively taken from a normal individual and a patient suffering for a multiple and frozen for storage were thawed by returning them to room temperature. 10 µl thereof was taken and added to 2 ml of distilled water containing 0.01% of dodecyltrimethyl ammonium bromide and adequately mixed using a Voltex mixer to obtain sample solutions. 10 µl therefor was then added to test tubes, and was diluted by the addition of 40 µl of PBS solution (pH 7.4) containing 2% BSA. Next, one bead having mouse anti-human medullasin monoclonal antibody (3F03) immobilized thereto and 350 µl of PBS solution containing 2% BSA and containing HRP-labelled mouse anti-human medullasin antibody (2E04) in a concentration of 0.2 µg/ml was added to each test tube followed by incubation at a temperature of 37° C. for 30 minutes. Next, washing, enzyme reaction and reaction termination were carried out by exactly the same operations as in the preparation of the calibration curves described earlier. The absorbance at a wavelength of 420 nm was then measured using a spectrophotometer, and the human medullasin concentration was determined from the calibration curve. The measurement operations starting from the sample dilution treatment were carried out for each 5 times for the purpose of studying the reproducibility of the measurements. As a result, it was confirmed that the human medullasin concentration measured for the blood samples showed extremely good reproducibility as shown in Table 3.

TABLE 3

Measured values for human medullasin in blood

| Measurement | Measured Value (µg/ml) | |
| --- | --- | --- |
| Number | Normal Individual | Patient |
| 1 | 8.3 | 39.6 |
| 2 | 8.1 | 38.8 |
| 3 | 8.3 | 39.2 |
| 4 | 8.4 | 40.1 |
| 5 | 7.9 | 39.5 |
| Average | 8.2 | 39.4 |
| Variation Coefficient (%) | 2.4 | 1.2 |

Comparative Example 2
Measurement of Medullasin in Clinical Sample Enzyme Immunoassay Blood samples which had been respectively taken from a normal individual and a patient suffering from multiple sclerosis patient and frozen for storage were thawed by returning them to room temperature. 10 µl thereof was taken and added to 2 ml of PBS solution (pH 7.4) and uniformly mixed to obtain a sample solution. 10 µl thereof was then added to test tubes, and was diluted by the addition of 40 µl of PBS solution (pH 7.4) containing 2% BSA. Next, one bead having mouse anti-human medullasin monoclonal antibody (3F03) immobilized thereto and 350 µl of PBS solution containing 2% BSA and containing HRP-labelled mouse anti-human medullasin monoclonal antibody (2E04) in a concentration of 0.2 µg/ml was added to these test tubes followed by incubation at a temperature of 37° C. for 30 minutes. Next, washing, enzyme reaction and reaction termination were carried out by exactly the same operations as in the preparation of the calibration curves described earlier. The absorbance at a wavelength of 420 nm was then measured using a spectrophotometer, and the human medullasin concentrations were determined from the calibration curve. The measurement operations starting from the sample dilution treatment were carried out for each 5 times for the purpose of studying the reproducibility of the measurements. As a result, it was confirmed that the human medullasin concentration measured for the blood samples gave data whose reproducibility could not be described as good as shown in Table 4.

TABLE 4

Measured values for human medullasin in blood

| Measurement | Measured Value (µg/ml) | |
| --- | --- | --- |
| Number | Normal Individual | Patient |
| 1 | 7.4 | 25.8 |
| 2 | 6.8 | 30.4 |
| 3 | 6.2 | 32.7 |
| 4 | 7.6 | 23.9 |
| 5 | 5.9 | 29.1 |
| Average | 6.8 | 28.4 |
| Variation Coefficient (%) | 10.9 | 12.5 |

Example 4
Calculation of Human Medullasin Value in Blood Sample and Disease Diagnosis Blood samples which had been respectively taken from normal individual, a patient suffering from multiple sclerosis and a patient suffering from a non-inflammatory nervous disease and frozen for storage were thawed by returning them to room temperature. 10 µl thereof was taken and added to 2 ml of distilled water (osmotic pressure=0 mOsm/kg.$H_2O$) and adequately mixed using a Voltex mixer to obtain sample solutions. 10 µl thereof was then added to test tubes, and was diluted by the addition of 390 µl of PBS solution (pH 7.4) containing 2% BSA. Next, one bead having mouse anti-human medullasin monoclonal antibody (3F03) immobilized thereto was added to each test tube followed by incubation at a temperature of 37° C. for 30 minutes. After removal of the solution in the test tubes by aspiration, they were washed with physiological saline solution. The test tubes were filled with 400 µl of PBS solution containing 2% BSA and containing HRP-labelled mouse anti-human medullasin monoclonal antibody (2E04) in a concentration of 0.2 µg/ml followed by incubation at a temperature of 37° C. for 30 minutes. Next, washing, enzyme reaction and reaction termination were carried out by exactly the same operations as in the preparation of the calibration curves described earlier. The absorbance at a wavelength of 420 nm was then measured using a spectrophotometer, and the human medullasin concentrations were determined from the calibration curve.

Figure 3:
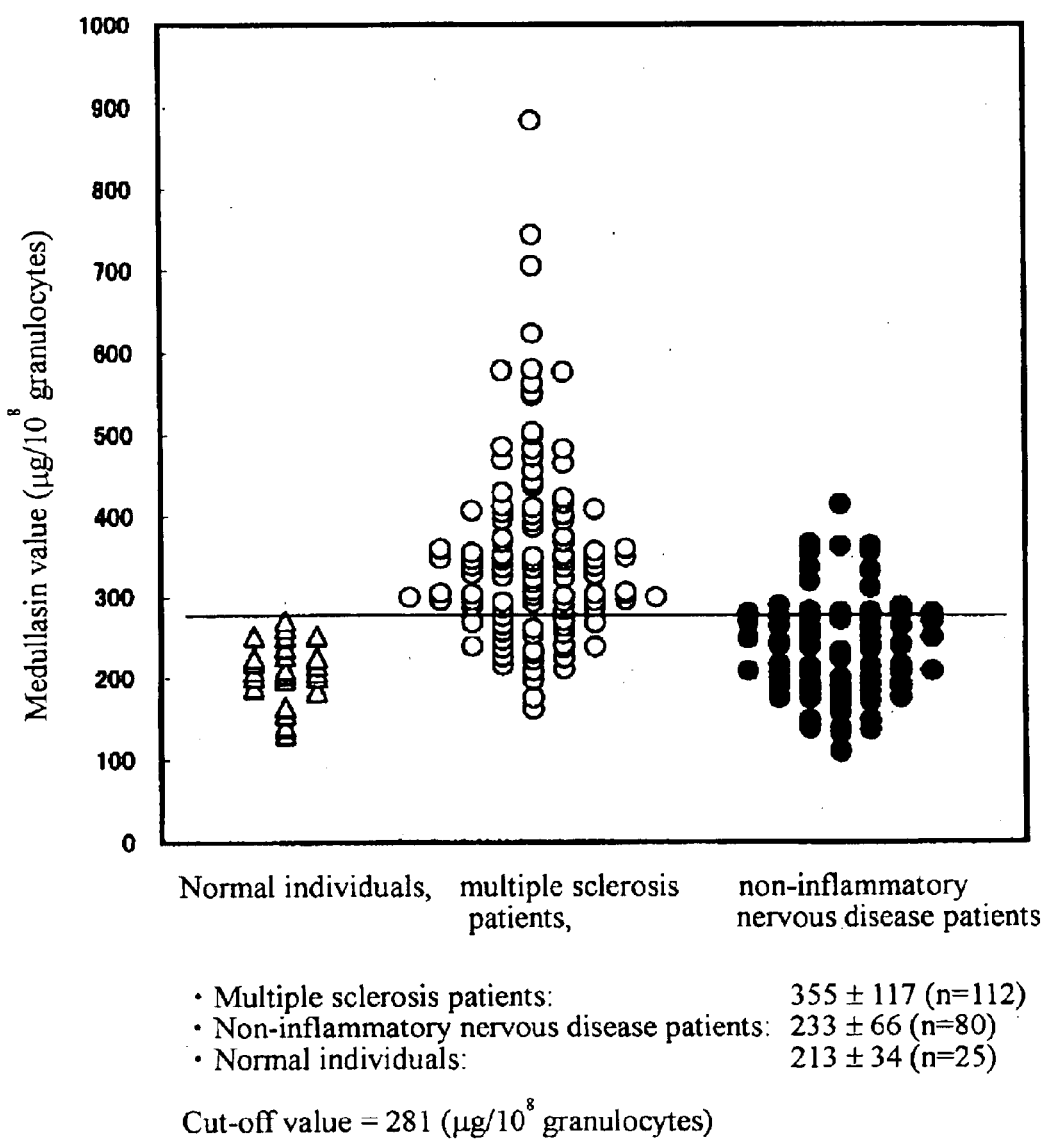
FIG. 3 shows human medullasin values in blood samples ($\mu g/10^8$ granulocytes) plotted separately for normal individuals, patients suffering from multiple sclerosis and patients suffering from non-inflammatory nervous diseases.

Human medullasin values ($\mu g/10^8$ granulocytes) showing the amount of medullasin in $10^8$ granulocytes were calculated from the human medullasin concentration and the number of granulocytes measured using each blood sample, and are shown in FIG. 3.

FIG. 3 shows a comparison of the respective medullasin values for normal individuals, multiple sclerosis patients and patients suffering from non-inflammatory nervous diseases. The following results are obtained from the figure.

| | |
|---|---|
| • Multiple sclerosis patients: | 355 ± 117 (n = 112) |
| • Non-inflammatory nervous disease patients: | 233 ± 66 (n = 80) |
| • Normal individuals: | 213 ± 34 (n = 25) |

These results were compared with a cut-off value (281 $\mu g/10^8$ granulocytes) and classed as positive or negative. The numbers of each and the positive percentages are shown in Table 5.

TABLE 5

Human medullasin values in clinical blood samples

| Sample | Number of Positives | Number of Negatives | Positive Percentage |
|---|---|---|---|
| Multiple sclerosis patients | 85 | 27 | 75.8 |
| Non-inflammatory disease patients | 13 | 67 | 16.3 |
| Normal individuals | 0 | 25 | 0.0 |

From the above results, it is observed that the diagnosis of multiple sclerosis according to the medullasin value in the blood is a diagnostic method of high reliability. Furthermore, the following results were obtained after classifying the medullasin value levels for multiple sclerosis patients according to male or female (see FIG. 4) and according to different ages (see FIG. 5).

Male/Female

| • Multiple sclerosis patients | |
|---|---|
| Female: | 351 ± 107 (n = 78) |
| Male: | 367 ± 143 (n = 34) |
| • Normal individuals: | 214 ± 34 (n = 24) |
| • Cut-off value: | 281 ($\mu g/10^8$ granulocytes) |

By Age

| • Multiple sclerosis patients | |
|---|---|
| 10–19: | 421 ± 154 (n = 9) |
| 20–29: | 329 ± 94 (n = 26) |
| 30–39: | 357 ± 104 (n = 30) |
| 40–49: | 330 ± 157 (n = 17) |
| 50 and over: | 375 ± 125 (n = 21) |
| • Normal individuals: | 213 ± 34 (n = 25) |
| • Cut-off value: | 281 ($\mu g/10^8$ granulocytes) |

These results show that no difference is observed between male and female and that no difference is observed according to age.

EFFECT OF THE INVENTION

With the invention as described above, it is possible to immunologically measure the content of human medullasin in a blood sample accurately and with good reproducibility. Furthermore, the diagnosis of the onset of multiple sclerosis or the extent or the state the disease can be carried out by blood diagnosis for chronic inflammatory diseases, particularly multiple sclerosis, using the measured value of the human medullasin content in blood.

We claim:

1. A method of immunologically measuring the human medullasin content in blood comprising the following steps (a) and (b):
   (a) breaking up the leukocytes in a blood sample by contacting said blood sample with the following aqueous liquid (i) or an aqueous liquid mixture of (i) and (ii)
      (i) an aqueous liquid, which contains 0.05 mole % or more or 0.005 mole % or less of a solute, having an osmotic pressure of 250 mOsm/kg.$H_2O$ or less or an aqueous liquid having an osmotic pressure of 310 mOsm/kg.$H_2O$ or more;
      (ii) an aqueous liquid comprising a hemolysate; and
   (b) immunologically determining content of human medullasin in said blood sample by a method comprising contacting the blood sample containing said human medullasin released from the leukocytes broken up in said step (a) with an anti-human medullasin monoclonal antibody immobilized to an insoluble carrier in the presence of a labeled anti-human medullasin monoclonal antibody to form a sandwich complex and to capture the human medullasin on a labeled immuno complex by an antigen-antibody reaction, and then determining the amount of activity of the label material in said complex.

2. The method of immunologically measuring the human medullasin content in blood according to claim 1, wherein said aqueous liquid (i) is a buffer solution and/or distilled water that may include a water-soluble organic solvent.

3. The method of immunologically measuring the human medullasin content in blood according to claim 1, wherein said aqueous liquid (i) is an aqueous solution containing a water-soluble substance selected from the group consisting of inorganic acid salts, organic acid salts, sugars, sugar alcohols, amino acids and protein substances.

4. The method of immunologically measuring the human medullasin content in blood according to claim 1, wherein the amount of said aqueous liquid (i) used is 50 to 100000 times that of the blood sample in terms of volume units.

5. The method of immunologically measuring the human medullasin content in blood according to claim 1 wherein said aqueous liquid (ii) is an aqueous solution of a surfactant.

6. The method of immunologically measuring the human medullasin content in blood according to claim 5, wherein said aqueous liquid (ii) is an aqueous solution of at least one type of hemolysate selected from the group consisting of higher fatty acid salts, alkylaryl sulphonates, alkyl sulphonates, alkyl sulphate ester salts, alkyl pyridinium salts, polyoxyethylene alkylphenyl ethers, polyoxyethylenealkylethers, polyoxyethylene sorbitan fatty acid esters and alkyl betaines.

7. The method of immunologically measuring the human medullasin content in blood according to claim 1 wherein the amount of aqueous liquid (ii) used is 50 times to 100000 times that of the blood sample in terms of volume units.

8. The method of immunologically measuring the human medullasin content in blood according to claim 1 wherein said step (b) of immunologically determining the content of human medullasin in said blood sample comprises sandwiching said human medullasin in said blood sample between an anti-human medullasin monoclonal antibody immobilized to an insoluble carrier and a labeled anti-human medullasin monoclonal antibody to form a complex by an antigen-antibody reaction, and determining the amount of label in said complex.

9. The method of immunologically measuring the human medullasin content in blood according to claim 1, wherein the aqueous liquid mixture of (i) and (ii) is used in step (a).

10. The method of immunologically measuring the human medullasin content in blood according to claim 1, wherein the aqueous liquid (i) is used in step (a).

11. A method of immunologically measuring the human medullasin content in blood comprising the following steps (a) and (b):
(a) breaking up the leukocytes in a blood sample by contacting said blood sample with the following aqueous liquid (i) or an aqueous liquid mixture of (i) and (ii)
    (i) an aqueous liquid having an osmotic pressure of 250 mOsm/kg.$H_2O$ or less or an aqueous liquid having an osmotic pressure of 310 mOsm/kg.$H_2O$ or more;
    (ii) an aqueous liquid comprising a hemolysate selected from the group consisting of higher fatty acid salts, alkylaryl sulphonates, alkyl sulphonates, alkyl sulphate ester salts, alkyl pyridinium salts, polyoxyethylene alkylphenyl ethers, polyoxyethylenealkyl-ethers, polyoxyethylene sorbitan fatty acid esters and alkyl betaines; and
(b) immunologically determining content of human medullasin in said blood sample by a method comprising contacting the blood sample containing said human medullasin released from the leukocytes broken up in said step (a) with an anti-human medullasin monoclonal antibody immobilized to an insoluble carrier in the presence of a labeled anti-human medullasin monoclonal antibody to form a sandwich complex and to capture the human medullasin on a labeled immuno complex by an antigen-antibody reaction, and then determining the amount of activity of the label material in said complex.

12. The method of immunologically measuring the human medullasin content in blood according to claim 11, wherein the aqueous liquid contains 0.05 mole % or more or 0.005 mole % or less of a solute.

13. The method of immunologically measuring the human medullasin content in blood according to claim 11, wherein the aqueous liquid mixture of (i) and (ii) is used in step (a).

14. The method of immunologically measuring the human medullasin content in blood according to claim 11, wherein the aqueous liquid (i) is used in step (a).

* * * * *